(12) United States Patent
Matsumoto et al.

(10) Patent No.: US 9,542,586 B2
(45) Date of Patent: Jan. 10, 2017

(54) PATTERN INSPECTION APPARATUS AND PATTERN INSPECTION METHOD

(75) Inventors: Eiji Matsumoto, Kanagawa (JP); Nobutaka Kikuiri, Tokyo (JP); Hideo Tsuchiya, Tokyo (JP)

(73) Assignee: NuFlare Technology, Inc., Numazu-shi (JP)

(*) Notice: Subject to any disclaimer, the term of this patent is extended or adjusted under 35 U.S.C. 154(b) by 358 days.

(21) Appl. No.: 13/572,972

(22) Filed: Aug. 13, 2012

(65) Prior Publication Data

US 2013/0044205 A1 Feb. 21, 2013

(30) Foreign Application Priority Data

Aug. 18, 2011 (JP) ................................. 2011-178877

(51) Int. Cl.
| | | |
|---|---|---|
| G03F 7/20 | (2006.01) | |
| G01N 21/956 | (2006.01) | |
| G06K 9/00 | (2006.01) | |
| H04N 7/18 | (2006.01) | |
| G01B 11/02 | (2006.01) | |
| G01N 21/95 | (2006.01) | |
| H01L 21/66 | (2006.01) | |
| G03F 1/84 | (2012.01) | |

(52) U.S. Cl.
CPC ............. *G06K 9/00* (2013.01); *G01B 11/02* (2013.01); *G01N 21/95* (2013.01); *G01N 21/95607* (2013.01); *G03F 1/84* (2013.01); *G03F 7/707* (2013.01); *G03F 7/70616* (2013.01); *H01L 22/00* (2013.01); *H04N 7/18* (2013.01); *G01B 2210/56* (2013.01); *G01N 2021/95615* (2013.01); *H01L 2924/0002* (2013.01)

(58) Field of Classification Search
USPC .......................................................... 348/86
See application file for complete search history.

(56) References Cited

U.S. PATENT DOCUMENTS

| | | | |
|---|---|---|---|
| 7,300,725 B2 | 11/2007 | Watson et al. | |
| 7,970,577 B2 * | 6/2011 | Mangan | G03F 1/0092 |
| | | | 355/53 |
| 2010/0074511 A1* | 3/2010 | Tamamushi et al. | 382/141 |

FOREIGN PATENT DOCUMENTS

| | | |
|---|---|---|
| JP | 3824542 | 7/2006 |
| JP | 2010-97168 | 4/2010 |

OTHER PUBLICATIONS

U.S. Appl. No. 13/705,663, filed Dec. 5, 2012, Tsuchiya, et al.

(Continued)

*Primary Examiner* — Mikhail Itskovich
(74) *Attorney, Agent, or Firm* — Oblon, McClelland, Maier & Neustadt, L.L.P.

(57) ABSTRACT

A pattern inspection method according to one aspect of the present invention includes generating a first positional deviation amount map by using data acquired by a pre-scan, generating a second positional deviation amount map by using data acquired by a full scan, generating a first positional deviation difference map by calculating a difference between the first positional deviation amount map and the second positional deviation amount map, generating a third positional deviation amount map from the first positional deviation difference map and the second positional deviation amount map, and judging existence of a value exceeding an allowable value, in values defined by the third positional deviation amount map.

20 Claims, 9 Drawing Sheets

(56) References Cited

OTHER PUBLICATIONS

U.S. Appl. No. 13/768,392, filed Feb. 15, 2013, Inoue et al.
U.S. Appl. No. 13/792,364, filed Mar. 11, 2013, Inoue et al.
U.S. Appl. No. 14/607,483, filed Jan. 28, 2015, Kikuiri.

* cited by examiner

PATTERN INSPECTION APPARATUS AND PATTERN INSPECTION METHOD

CROSS-REFERENCE TO RELATED APPLICATION

This application is based upon and claims the benefit of priority from the prior Japanese Patent Application No. 2011-178877 filed on Aug. 18, 2011 in Japan, the entire contents of which are incorporated herein by reference.

BACKGROUND OF THE INVENTION

Field of the Invention

The present invention relates to a pattern inspection apparatus and a pattern inspection method. For example, it relates to an inspection apparatus that inspects a pattern by comparing an optical image of a pattern image, which is obtained by irradiating illumination light, with a reference image, which is generated from configuration data etc., and relates to a method therefor.

Description of Related Art

In recent years, with the advance of high integration and large capacity of a large scale integrated circuit (LSI), the line width (critical dimension) required for a circuit of a semiconductor element is becoming narrower and narrower. Such semiconductor elements are manufactured by exposing (transferring) a pattern onto a wafer to form a circuit by means of a reduced projection exposure apparatus, which is known as a stepper, by using an original or "master" pattern (also called a mask or a reticle, and will be generically referred to as a mask hereinafter) with a circuit pattern formed thereon. Therefore, in manufacturing a mask for transferring such a fine circuit pattern onto a wafer, a pattern writing apparatus using electron beams capable of writing or "drawing" fine circuit patterns needs to be employed. Pattern circuits may be written directly on a wafer by the pattern writing apparatus. Alternatively, a laser beam writing apparatus which uses laser beams in place of electron beams for writing a pattern is under development.

Since the LSI manufacturing requires a tremendous amount of manufacturing cost, it is crucial to improve its yield. However, as typified by a 1 gigabit DRAM (Dynamic Random Access Memory), the scale of a pattern configuring an LSI has been changing from on the order of submicron to on the order of nanometer. One of major factors that decrease the yield of the LSI manufacturing is a pattern defect of a mask used when exposing (transferring) a fine pattern onto a semiconductor wafer by the photolithography technology. In recent years, with miniaturization of an LSI pattern formed on a semiconductor wafer, dimension to be detected as a pattern defect have become extremely small. Thus, a pattern inspection apparatus for inspecting a defect of a transfer mask used in manufacturing LSI needs to be highly accurate.

Meanwhile, with development of multimedia technology, the size of LCD (Liquid Crystal Display) substrate is becoming larger, e.g., 500 mm×600 mm or greater, and the size of a pattern such as a TFT (Thin Film Transistor) or the like formed on the liquid crystal substrate is becoming finer. Therefore, it is increasingly required that an extremely small defect of a pattern should be inspected in a large range. For this reason, development of a pattern inspection apparatus that efficiently and short-timely inspects a defect of a photomask used when manufacturing patterns of a large area LCD and a large-area LCD is urgently required.

As an inspection method, there is known a method of comparing an optical image of a pattern formed on a target object or "sample", such as a lithography mask, imaged at a predetermined magnification by using a magnifying optical system with design data or an optical image obtained by imaging the same pattern on the target object. For example, the following is known as pattern inspection methods: die-to-die inspection method that compares data of optical images of identical patterns at different positions on the same mask, and die-to-database inspection method that inputs, into the inspection apparatus, writing data (design pattern data) which is generated by converting pattern-designed CAD data to a writing apparatus specific format for input when writing a pattern on the mask, generates design image data (reference image) based on the input writing data, and compares the generated design image data with an optical image (serving as measurement data) obtained by imaging the pattern. According to the inspection method of the inspection apparatus, a target object is placed on the stage so that a light flux may scan the object by the movement of the stage in order to perform an inspection. Specifically, the target object is irradiated with a light flux from the light source and the illumination optical system. Light transmitted through the target object or reflected therefrom is focused on a sensor through the optical system. An image captured by the sensor is transmitted as measurement data to the comparison circuit. In the comparison circuit, after position alignment of the images, measurement data and reference data are compared with each other in accordance with an appropriate algorithm. If there is no matching between the measurement data and the reference data, it is judged that a pattern defect exists.

While with the advance in miniaturization of patterns, it continues to use the photolithography technology that forms a circuit by exposing and transferring a pattern onto a wafer by means of a reduced projection exposure device using a mask serving as a pattern original. Then, in order to increase a manufacturing yield of wafers, the allowable accuracy range (margin) with respect to a pattern defect of a mask and the allowable variation range (margin) with respect to process conditions in exposing and transferring are becoming tight. Until now, since the accuracy of dimension of a mask pattern has been kept high by having a tight range of tolerance values with respect to a shape defect, even when a variation margin of process conditions is somewhat wide, the width has been compensated for by the tightness of the accuracy of mask pattern dimension. However, recently, it is increasingly required for quality of a mask to be inspected to have uniformity of pattern position accuracy and pattern dimension errors on the whole surface of the mask in addition to having the accuracy that figures composing a pattern are formed exactly in accordance with the design respectively. Conventionally, the quality control of the uniformity of a mask surface has been performed by grasping errors of extension and contraction, parallel shifts, and local variation which are measured based on positions of cross marks arranged at suitable intervals in the mask pattern, by using a dedicated measuring device, in order to measure a variation amount of each point coordinates which should be an ideal grid.

Mask defect inspection usually performed is designed to detect a pattern shape defect, and thereby, a defect dimension to be detected becomes fine in accordance with the miniaturization of mask patterns. Accordingly, the detection needs to be performed by using a detection optical system of high magnification, and the inspection time required for inspecting a defect of the whole mask surface has come up to several hours, for example. Then, during such several hours of mask defect inspection, there occurs a problem in that a pattern position and a pattern dimension obtained based on a measured result vary in the mask surface by a thermal expansion of the mask to be inspected, which is generated from the storage of energy of inspection light irradiated on the mask, by a measurement error of the stage position measuring system, which is generated from a change of air current inside the inspection apparatus or various heat sources in the apparatus, and so on. Consequently, the uniformity of pattern position accuracy and the uniformity of pattern dimension errors in the whole surface of the mask are degraded, and the level of such degradation of the uniformity has become too high to ignore for the quality precision of the mask. Thus, to inspect the uniformity is an issue to be solved for assuring the reliability of the inspection apparatus and the mask to be inspected.

A pattern dimension error can be calculated, for example, by detecting edges at both the ends of a pattern from a measured optical image, obtaining the distance between the edge pair in order to measure a line width dimension of the measured optical image, detecting edges at both the ends of a pattern from a reference data image, and obtaining the distance between the edge pair in order to measure a line width dimension of the reference data image, so that the pattern dimension error is calculated by obtaining a difference between the line width dimensions (refer to, e.g., Japanese Patent Application Laid-open (JP-A) No. 3824542). However, the dimension error calculated herein includes, as described above, an error due to the inspection apparatus, such as a thermal expansion of the inspection mask, which is generated from the storage of energy of inspection light irradiated on the mask, and a measurement error of the stage position measuring system, which is generated from a change of air current inside the inspection apparatus or various heat sources in the apparatus. Therefore, there is a problem that it cannot be known whether the dimension error belongs to a pattern formed on the mask or the dimension error is due to the inspection apparatus.

BRIEF SUMMARY OF THE INVENTION

In accordance with one aspect of the present invention, an inspection apparatus includes a stage on which an inspection target object with a plurality of figure patterns formed thereon is placed and which is movable, a light source configured to emit an inspection light, a sensor configured to capture an optical image of the plurality of figure patterns formed on the inspection target object by using the inspection light while moving relatively to the stage, a first image acquisition control unit configured, with respect to a plurality of discrete small regions in a plurality of small regions made by virtually dividing a whole of an inspection region of the inspection target object into strip-like regions, to control so as to acquire an optical image in each of the plurality of discrete small regions in order, while relatively moving the sensor and the stage without performing imaging with respect to a region located between each of the plurality of discrete small regions, a second image acquisition control unit configured to control so as to acquire an optical image in each small region in the whole of the inspection region of the inspection target object in order while relatively moving the sensor and the stage, a first positional deviation amount calculation unit configured to calculate a first positional deviation amount between a dimension of a figure in each optical image acquired when capturing images of the plurality of discrete small regions and a dimension of a figure in a reference image corresponding to the each optical image, a first positional deviation amount map generation unit configured to generate a first positional deviation amount map of the whole of the inspection region by using the first positional deviation amount of each of the plurality of discrete small regions, a second positional deviation amount calculation unit configured to calculate a second positional deviation amount between a dimension of a figure in each optical image acquired when capturing images of the whole of the inspection region and a dimension of a figure in a reference image corresponding to the each optical image, a second positional deviation amount map generation unit configured to generate a second positional deviation amount map of the whole of the inspection region by using the second positional deviation amount, a first positional deviation difference map generation unit configured to generate a first positional deviation difference map by calculating a difference between the first positional deviation amount map and the second positional deviation amount map, a third positional deviation amount map generation unit configured to generate a third positional deviation amount map by calculating a difference between the second positional deviation amount map and the first positional deviation difference map, a positional deviation amount judging unit configured to judge existence of a value exceeding an allowable value, in values defined by the third positional deviation amount map, and an output unit configured to output a judgment result.

In accordance with another aspect of the present invention, a pattern inspection method includes generating a first positional deviation amount map by using data acquired by a pre-scan, generating a second positional deviation amount map by using data acquired by a full scan, generating a first positional deviation difference map by calculating a difference between the first positional deviation amount map and the second positional deviation amount map, generating a third positional deviation amount map from the first positional deviation difference map and the second positional deviation amount map, and judging existence of a value exceeding an allowable value, in values defined by the third positional deviation amount map.

Moreover, in accordance with another aspect of the present invention, a pattern inspection method includes generating a first dimension error amount map by using data acquired by a pre-scan, generating a second dimension error amount map by using data acquired by a full scan, generating a first dimension error amount difference map by calculating a difference between the first dimension error amount map and the second dimension error amount map, generating a third dimension error amount map from the first dimension error amount difference map and the second dimension error amount map, and judging existence of a value exceeding an allowable value, in values defined by the third dimension error amount map.

DETAILED DESCRIPTION OF THE INVENTION

As a quality of a mask to be inspected, uniformity of pattern position accuracy and uniformity of pattern dimension errors are required in addition to the accuracy that figures composing a pattern are formed exactly in accordance with the design respectively. However, a pattern position and a pattern dimension obtained based on measured results vary in the mask surface by a thermal expansion of the mask to be inspected, which is generated from the storage of energy of inspection light irradiated on the mask, by a measurement error of the stage position measuring system, which is generated from a change of air current inside the inspection apparatus or various heat sources in the apparatus, and so on.

In Embodiments described below, there will be explained an inspection apparatus and a method thereof that can inspect at least one of uniformity of position accuracy and uniformity of dimension error of a pattern itself formed on a mask.

Embodiment 1

Figure 1:
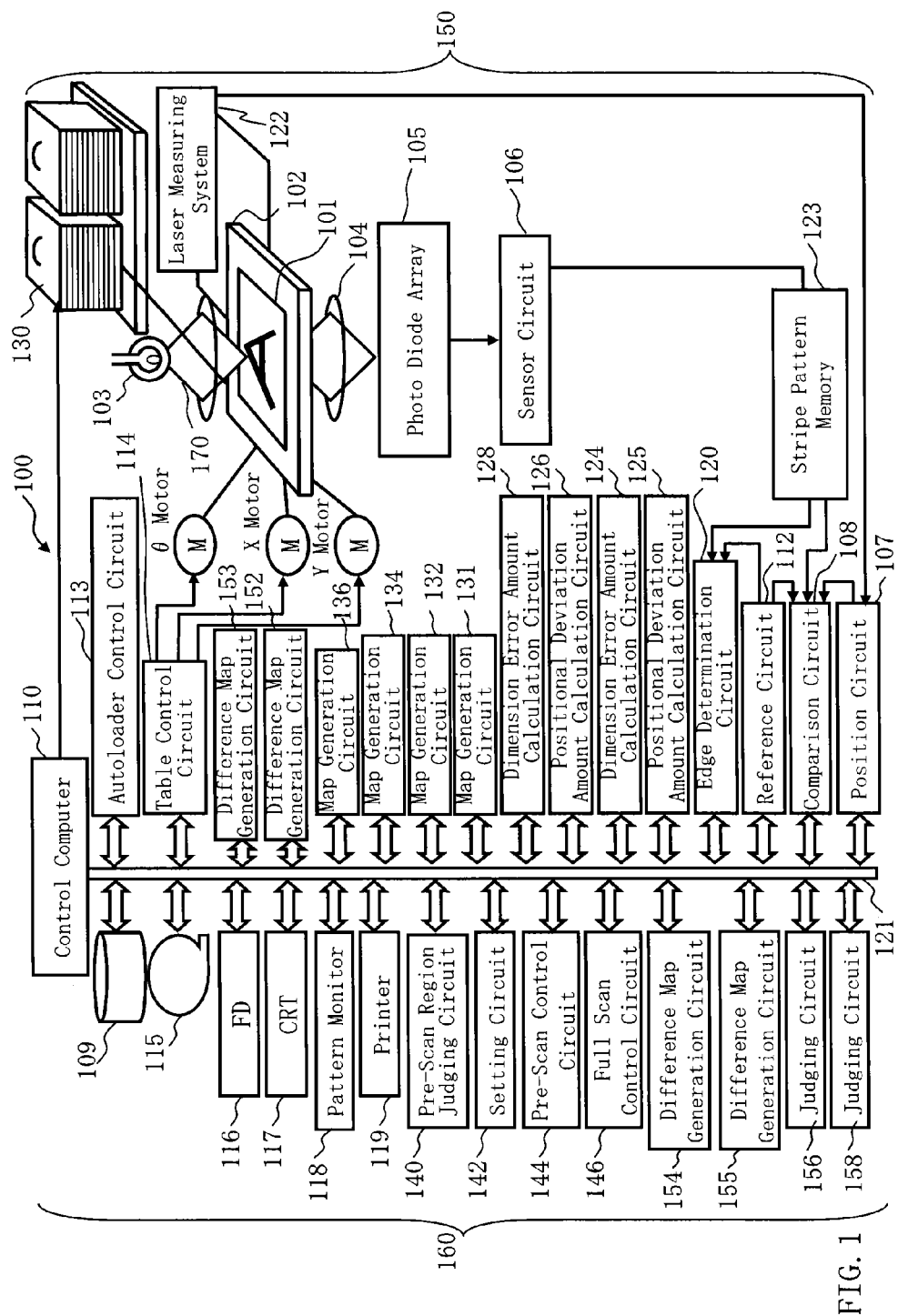
FIG. 1 is a schematic diagram showing a configuration of a pattern inspection apparatus according to Embodiment 1.

FIG. 1 is a schematic diagram showing a configuration of a pattern inspection apparatus according to Embodiment 1. In FIG. 1, an inspection apparatus 100 for inspecting a defect of a target object, such as a mask, includes an inspection unit 150 and a control system circuit 160. The inspection unit 150 includes a light source 103, an XYθ table 102, an illumination optical system 170, a magnifying optical system 104, a photo diode array 105 (an example of a sensor), a sensor circuit 106, a stripe pattern memory 123, a laser measuring system 122, and an autoloader 130. In the control system circuit 160, a control computer 110 is connected, through a bus 121, to a position circuit 107, a comparison circuit 108, a reference circuit 112, an autoloader control circuit 113, a table control circuit 114, a magnetic disk drive 109, a magnetic tape drive 115, a flexible disk drive (FD) 116, a CRT 117, a pattern monitor 118, a printer 119, an edge determination circuit 120, positional deviation amount calculation circuits 125 and 126, dimension error amount calculation circuits 124 and 128, map generation circuits 131, 132, 134, and 136, a pre-scan region judging circuit 140, a setting circuit 142, a pre-scan control circuit 144, a full scan control circuit 146, difference map generation circuits 152, 153, 154, and 155, and judging circuits 156 and 158. Moreover, the sensor circuit 106 is connected to the stripe pattern memory 123 which is connected to the comparison circuit 108 and the edge determination circuit 120.

The XYθ table 102 is driven by an X-axis motor, a Y-axis motor, and a θ-axis motor. The XYθ table 102 serves as an example of the stage. FIG. 1 shows structure elements necessary for describing Embodiment 1, and it should be understood that other structure elements generally necessary for the inspection apparatus 100 may also be included therein.

In the inspection apparatus 100, an inspection optical system of large magnification is composed of the light source 103, the XYθ table 102, the illumination optical system 170, the magnifying optical system 104, the photo diode array 105, and the sensor circuit 106. The XYθ table 102 is driven by the table control circuit 114 under the control of the control computer 110. The XYθ table 102 can be moved by a drive system such as a three-axis (X, Y, and θ) motor, which drives the XYθ table 102 in the X direction, the Y direction, and the θ direction. For example, a step motor can be used as each of these X, Y, and θ motors. The moving position of the XYθ table 102 is measured by the laser measuring system 122 and supplied to the position circuit 107. A photo-mask 101 on the XYθ table 102 is automatically conveyed from the autoloader 130 which is driven by the autoloader control circuit 113, and automatically ejected after the inspection.

The photo-mask 101 serving as an inspection target object, on which a plurality of figure patterns are formed, is placed on the XYθ table 102 that is movable in a horizontal direction and a rotating direction by the X-, Y-, and θ-axis motors. Then, the patterns formed on the photo-mask 101 are irradiated by a light (inspection light) of a wavelength of, or below, the ultraviolet region emitted from the suitable light source 103 through the illumination optical system 170. The light transmitted through the photo-mask 101 is focused on the photo diode array 105, via the magnifying optical system 104, as an optical image and enters thereinto. It is preferable to use, for example, a TDI (Time Delay Integration) sensor as the photo diode array 105.

Figure 2:
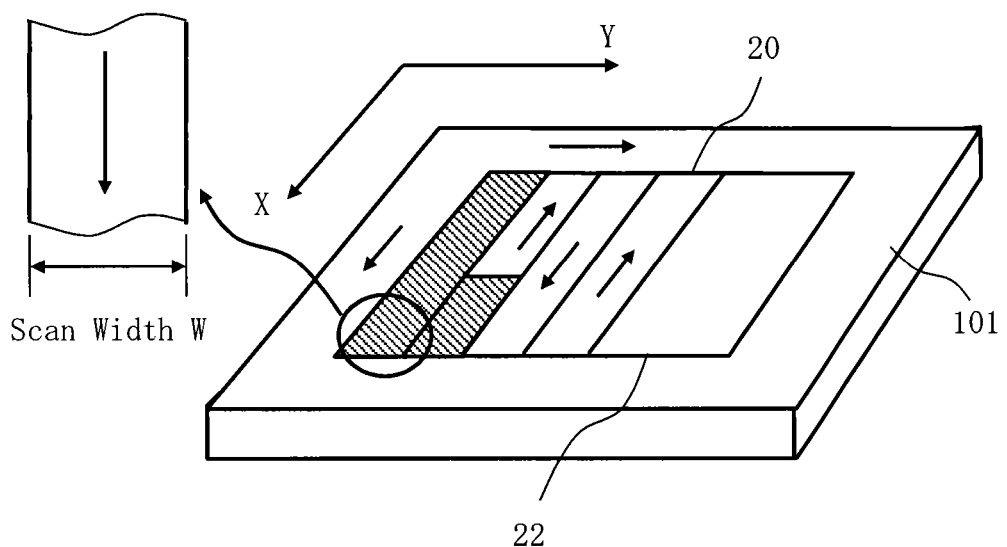
FIG. 2 is a schematic diagram describing a procedure for acquiring an optical image according to Embodiment 1.

FIG. 2 is a schematic diagram describing a procedure for acquiring an optical image according to Embodiment 1. An inspection region 22 is, as shown in FIG. 2, virtually divided into a plurality of strip-like inspection stripes 20 (an example of a small region or a stripe region) each having a scan width W in the Y direction, for example. The movement of the XYθ table 102 is controlled such that each divided inspection stripe 20 is scanned continuously. By the movement of the XYθ table 102, optical images are acquired by the photo diode array 105 which moves, relatively to the XYθ table 102, in the X direction continuously. That is, the photo diode array 105 continuously captures optical images each having a scan width W as shown in FIG. 2. In other words, the photo diode array 105, being an example of a sensor, captures optical images of a plurality of figure patterns formed on the photo-mask 101 by using an inspection light, while moving relatively to the movement of the XYθ table 102 (stage). According to Embodiment 1, after capturing an optical image in one inspection stripe 20, the photo diode array 105 similarly captures another optical image having the scan width W continuously at a position shifted in the Y direction by the scan width W, while moving in a direction reverse to the last image capturing direction. That is, the image capturing is repeated in the forward (FWD) to backward (BWD) direction, meaning going in a reverse direction when advancing and returning.

Then, the direction of the image capturing is not limited to repeating the forward (FWD) and backward (BWD) movement. It is also acceptable to capture an image from one direction with respect to each inspection stripe 20. For example, repeating a FWD and FWD movement may be sufficient, and alternatively, a BWD and BWD movement may also be sufficient. In the example of FIG. 2, the X direction is shown as the FWD direction and the −X direction is shown as the BWD direction, for example.

The pattern image focused on the photo diode array 105 is photoelectrically converted by each light receiving element of the photo diode array 105, and is further analog-to-digital (A/D) converted by the sensor circuit 106. Pixel data of each inspection stripe 20 is stored in the stripe pattern memory 123. Then, the pixel data is sent to the comparison circuit 108 and the edge determination circuit 120, with data which is output from the position circuit 107 and indicates the position of the photo-mask 101 on the XYθ table 102. Measurement data is 8-bit unsigned data, for example, and indicates a gray level (light intensity) of brightness of each pixel.

As described above, the inspection time required for inspecting a defect of a mask has come up to several hours, for example, two to six hours, and during such several hours of mask defect inspection, there occurs a problem in that a pattern position and a pattern dimension obtained based on a measured result vary in the mask surface by a thermal expansion of the photo-mask 101 to be inspected, which is generated from the storage of energy of an inspection light irradiated on the photo-mask 101, and alternatively or additionally, by a measurement error of the laser measuring system 122, which is generated from a change of air current inside the inspection apparatus 100 or various heat sources in the apparatus 100, and so on. Consequently, the uniformity of pattern position accuracy and the uniformity of pattern dimension errors in the whole surface of the mask are degraded, and the level of such degradation of the uniformity has become too high to ignore for the quality precision of the mask.

As a countermeasure to the problem, if the operation with respect to a mask defect inspection can be performed within a short time, it becomes possible to make the above-described variation due to the inspection apparatus 100 ignorably small. In other words, it becomes possible to perform the inspection in a state without the influence of a temperature change. Meanwhile, it is very difficult to acquire images of the whole surface of the inspection region 22 of the photo-mask 101 in a short time. Then, according to Embodiment 1, first of all, images only with respect to a plurality of discrete regions in the inspection region 22 of the photo-mask 101 are acquired within the time shorter than the time for acquiring images of the whole surface of the inspection region 22 of the photo-mask 101. Then, the above-described variation amount due to the inspection apparatus 100 is corrected by using the acquired images of a plurality of discrete regions.

Figure 3:
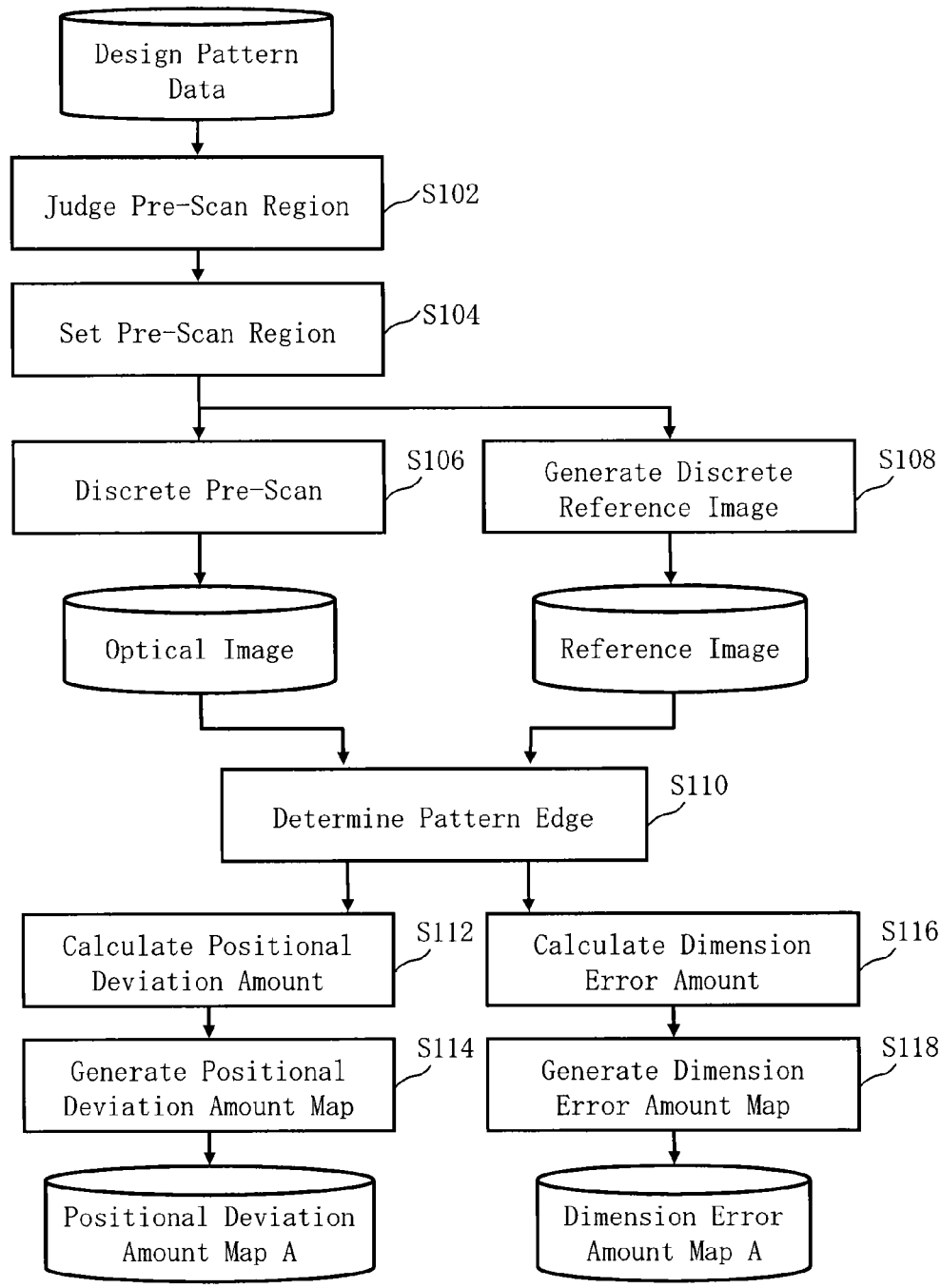
FIG. 3 is a flowchart showing a part of main steps of an inspection method according to Embodiment 1.

FIG. 3 is a flowchart showing a part of main steps of an inspection method according to Embodiment 1. In FIG. 3, there is shown each step of measuring a positional deviation amount and a dimension error by a pre-scan in the series of steps of the inspection method according to Embodiment 1. The method of measuring a positional deviation amount and a dimension error by a pre-scan according to Embodiment 1 executes a series of steps: a pre-scan region judgment step (S102), a pre-scan region setting step (S104), a discrete pre-scanning step (S106), a discrete reference image generation step (S108), a pattern edge determination step (S110), a positional deviation amount calculation step (S112), a positional deviation amount map generation step (S114), a dimension error amount calculation step (S116), and a dimension error amount map generation step (S118).

In the pre-scan region judgment step (S102), the pre-scan region judging circuit 140 judges, in a plurality of inspection stripes 20 made by virtually dividing the inspection region 22, whether a figure pattern exists in each of inspection stripes 20 equally distant from each other at predetermined intervals. The pre-scan region judging circuit 140 is an example of a judging unit.

Figure 4:
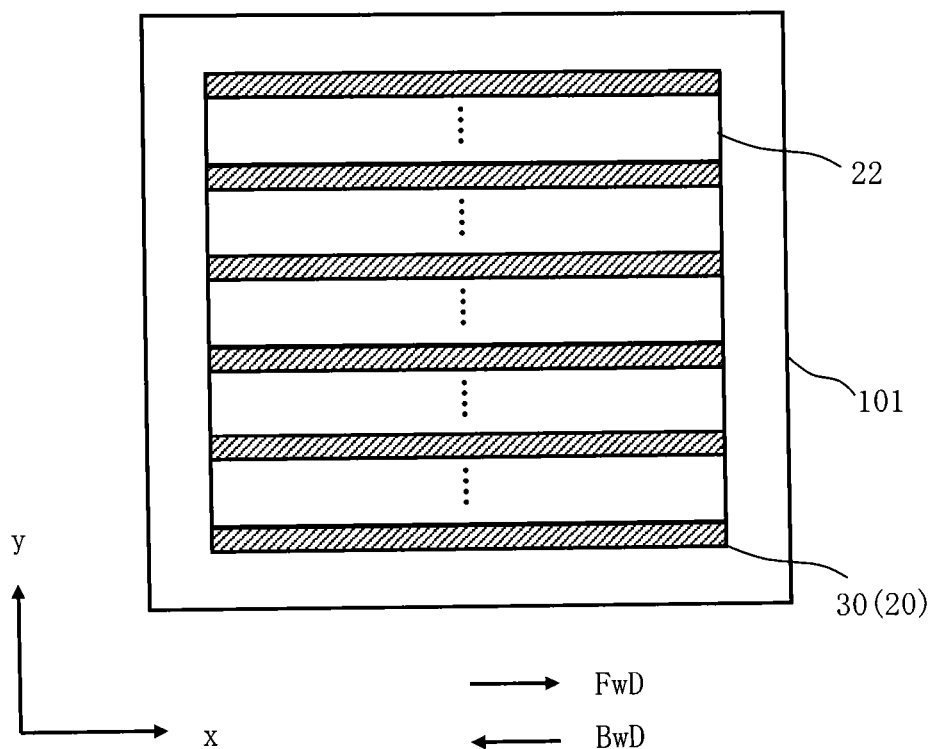
FIG. 4 is a schematic diagram showing an example of a pre-scan region according to Embodiment 1.

FIG. 4 is a schematic diagram showing an example of a pre-scan region according to Embodiment 1. In FIG. 4, as described above, the inspection region 22 of the photo-mask 101 is virtually divided into a plurality of inspection stripes 20. Then, a pre-scan region 30 to be pre-scanned is determined from a plurality of inspection stripes 20. As the pre-scan region 30, it is desirable to use some inspection stripes 20 which are discrete, and in this case, are equally distant from each other at predetermined intervals, in a plurality of inspection stripes 20. For example, it is preferable to equally divide the inspection region 22 into n (for example, ten) stripes in the Y direction, and to use the first inspection stripe 20 in the n divided stripes in the Y direction in each inspection region. That is, it is preferable such plural discrete inspection stripes 20 are used. Further, it is more preferable to set such that respective pre-scan regions 30 are equally distant from each other. By having pre-scan regions 30 which are discrete at equal intervals, bias of the inspection regions can be suppressed. Accordingly, a more accurate map to be described later can be obtained. However, there is a possibility that no figure pattern is formed in the inspection stripe 20 used as the pre-scan region 30. In the case of the inspection stripe 20 with no figure pattern being used as the pre-scan region 30, no pattern image is obtained by imaging, thereby no necessary information can be acquired. Then, first, the pre-scan region judging circuit 140 judges whether a figure pattern exists in each of the inspection stripes 20 which are discrete at predetermined equal intervals or not in a plurality of inspection stripes 20 obtained by virtually dividing the inspection region 22. As a method of checking whether a figure pattern exists or not, it is preferable, for example, in each mesh region of a stripe concerned, to perform processing similar to the processing of determining (detecting) a pattern edge pair of the pattern edge determination step (S110) to be described later, and to judge that a figure pattern does not exist when the number of detected pattern edge pairs is less than a predetermined number. However, it is not limited thereto.

In the pre-scan region setting step (S104), when a figure pattern exists in each of all the judged inspection stripes 20, the setting circuit 142 sets all the judged inspection stripes 20 as a plurality of discrete inspection stripes 20 (pre-scan regions 30). On the other hand, when a figure pattern does not exist in each of some or all of the judged inspection stripes 20, the setting circuit 142 searches and sets, instead of the inspection stripe 20 concerned with no figure pattern, an inspection stripe 20 in which a figure pattern exists and which is closest to the inspection stripe 20 concerned with no figure pattern. In other words, inspection stripes 20, each including a figure pattern, and inspection stripes 20, each of which is closest to an inspection stripe 20 concerned with no figure pattern and is used instead of the inspection stripe 20 concerned with no figure pattern, are set as a plurality of discrete inspection stripes 20 (pre-scan regions 30). The setting circuit 142 is an example of a setting unit. An optical image of a pattern can be obtained by setting the inspection stripe 20 with a figure pattern.

In the discrete pre-scanning step (S106), the pre-scan control circuit 144 controls each device to acquire optical images (measurement data) in order in a plurality of setted discrete inspection stripes 20 (pre-scan regions 30). In that case, the photo diode 105 and the XYθ table 102 are relatively moved without capturing images of the inspection stripe 20 located between the setted pre-scan regions 30. With respect to a plurality of pre-scan regions 30, image capturing is repeated, for example, in the FWD to BWD direction, meaning going in a reverse direction when advancing and returning. The pattern image focused on the photo diode array 105 is photoelectrically converted by each light receiving element of the photo diode array 105, and is further A/D (analog to digital) converted by the sensor circuit 106. Then, pixel data is temporarily stored in the stripe pattern memory 123 for each inspection stripe 20 (pre-scan region 30). Thereby, the time up to completing imaging of all the set pre-scan regions 30 can be shortened. Therefore, it is possible to greatly shorten the imaging time with respect to the whole surface of the inspection region 22, compared with the case of imaging each inspection stripe 20 in order. As a result, the energy storage amount of the inspection light irradiated on the photo-mask 101 decreases, and thereby, the thermal expansion of the photo-mask 101 can be suppressed. Moreover, the amount of heat emitted from the various heat sources in the inspection apparatus 100 can be reduced. Therefore, it is possible to suppress measurement errors of the stage position, which is generated from a change of air current inside the inspection apparatus 100 or heat emitted from various heat sources in the inspection apparatus 100. In other words, measurement errors due to the inspection apparatus 100 can be reduced. The pre-scan control circuit 144 is an example of the first image acquisition control unit. Then, the pixel data is sent to the edge determination circuit 120, with the data which indicates the position of the photo-mask 101 on the XYθ table 102 and which is output from the position circuit 107. The measurement data is 8-bit unsigned data, for example, and indicates a gray level (light intensity) of brightness of each pixel.

In the discrete reference image generation step (S108), the reference circuit 112 reads design data of a plurality of setted discrete inspection stripes 20 (pre-scan regions 30) from the magnetic disk drive 109 through the control computer 110. The read design data of the photo-mask 101 is converted into image data of binary values or multiple values to generate reference data (reference image). The reference data is 8-bit unsigned data, for example, and indicates a gray level (light intensity) of brightness of each pixel. Then, the reference data is sent to the edge determination circuit 120.

Figure 5:
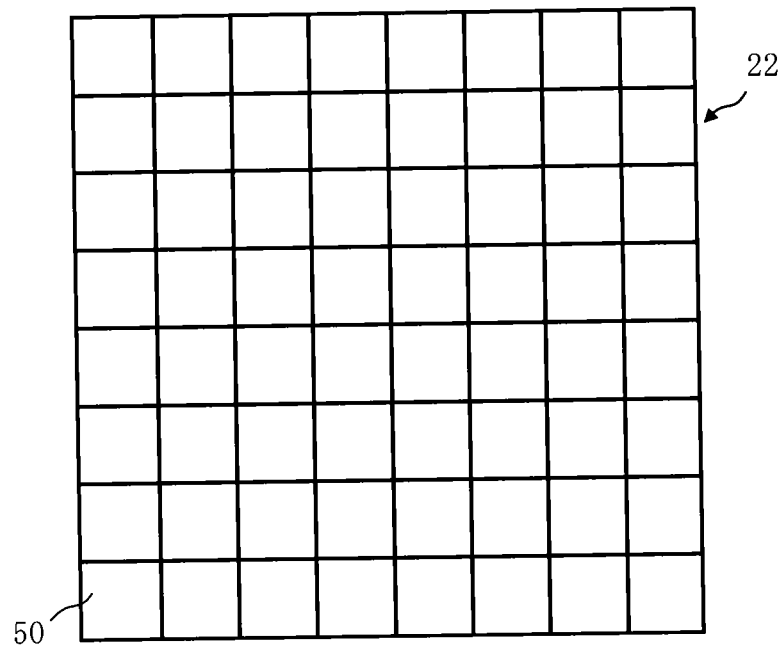
FIG. 5 is a schematic diagram for explaining an inspection region which has been divided into mesh regions according to Embodiment 1.

FIG. 5 is a schematic diagram for explaining an inspection region which has been divided into mesh regions according to Embodiment 1. The inspection region 22 of the photomask 101 is virtually divided into a plurality of mesh regions 50 by a grid of a predetermined quantization size. It is desirable that the size of the mesh region 50 is sufficiently smaller than the width of the inspection stripe 20. In other words, each inspection stripe 20 is divided into a plurality of mesh regions 50.

In the pattern edge determination step (S110), the edge determination circuit 120 determines, for each mesh region, edges of a pattern (figure) with respect to the X direction, the Y direction, and a diagonal 45 degree direction (including 45, 135, 225, and 315 degrees), in pattern images respectively located in the optical image obtained from the sensor and the reference image. Then, a pattern edge (side) and another pattern edge (side) being a pair configuring the edge part are determined. Thus, the edge determination circuit 120 determines (detects) a pattern edge pair. In other words, the edge determination circuit 120 determines (detects) sides at both the ends which are factors to determine the dimension of each figure.

In the positional deviation amount calculation step (S112), the positional deviation amount calculation circuit 125 calculates a positional deviation amount (a first positional deviation amount) between a dimension of a figure in each optical image acquired when capturing images of a plurality of discrete inspection stripes 20 (pre-scan regions 30) and a dimension of a figure in each reference image corresponding to the optical image concerned. The positional deviation amount calculation circuit 125 is an example of the first positional deviation amount calculation unit.

Figure 6A:
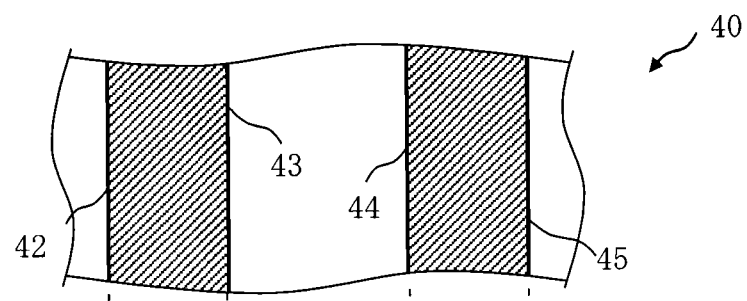
FIGS. 6A and 6B show examples of a pattern position and a pattern dimension according to Embodiment 1.
Figure 6B:
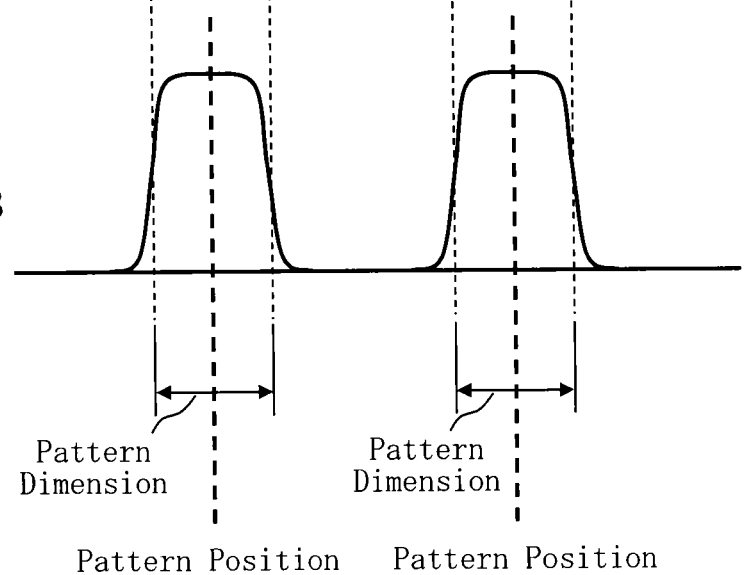

FIGS. 6A and 6B show examples of a pattern position and a pattern dimension according to Embodiment 1. FIG. 6A shows a top view of a pattern located in a partial region 40 in a mesh region. FIG. 6B shows an example of a dose profile corresponding to the pattern of FIG. 6A. Specifically, first, the positional deviation amount calculation circuit 125 determines (calculates), for each mesh region, a central position (coordinates) between the determined pattern edge pair 42 and 43 (or the pattern edge pair 44 and 45) in an optical image and a reference image respectively. The central position between such edges is defined to be the position (coordinates) of a pattern. Next, the positional deviation amount calculation circuit 125 calculates a difference between a pattern position acquired from an optical image and a corresponding pattern position acquired from a reference image. The difference is regarded as a positional deviation amount (a first positional deviation amount). Since a plurality of patterns are usually located in each mesh region, positional deviation amounts are respectively calculated in accordance with the number of a plurality of patterns. Then, according to Embodiment 1, statistical processing is performed for respective calculated values, and the mode value is defined to be a positional deviation amount (the first positional deviation amount) representing the mesh region 50.

In the positional deviation amount map generation step (S114), the map generation circuit 131 generates a positional deviation amount map (a first positional deviation amount map) of the whole of the inspection region 22 by using each positional deviation amount (the first positional deviation amount) in a plurality of discrete inspection stripes 20 (pre-scan regions 30). The map generation circuit 131 is an example of the first positional deviation amount map generation unit. Since here only the value of each mesh region of a plurality of discrete inspection stripes 20 (pre-scan regions 30) is held as data, the map generation circuit 131 performs approximation (fitting) for the obtained mesh region value by using a polynomial in order to presume and estimate a value of other mesh region without data. Then, with respect to mesh regions with data, corresponding mesh region values are respectively input. By contrast, with respect to other mesh regions without data, estimated values are respectively input. Thus, a positional deviation amount map (the first positional deviation amount map) of the whole of the inspection region 22 is generated. Fitting using a polynomial is performed in this case, however, it is not limited thereto, and a value of other mesh region without data may be interpolated by a linear interpolation. The generated positional deviation amount map (the first positional deviation amount map, a positional deviation amount map A) is stored in the magnetic disk drive 109, for example.

In the dimension error amount calculation step (S116), the dimension error amount calculation circuit 124 calculates a dimension error amount (a first dimension error amount) between a dimension of a figure in each optical image acquired when capturing images of a plurality of discrete inspection stripes 20 (pre-scan regions 30) and a dimension of a figure in each reference image corresponding to the optical image concerned. The dimension error amount calculation circuit 124 is an example of the first dimension error amount calculation unit. Specifically, first, the dimension error amount calculation circuit 124 calculates, for each mesh region, a distance between the determined pattern edge pair 42 and 43 (or the pattern edge pair 44 and 45) in an optical image and a reference image respectively. The distance between such edges is defined to be a pattern dimension. Next, the dimension error amount calculation circuit 124 calculates a difference between the pattern dimension acquired from an optical image and the dimension of the corresponding pattern acquired from a reference image. The difference is regarded as a dimension error amount (a first dimension error amount). Since a plurality of patterns are usually located in each mesh region, dimension error amounts are respectively calculated in accordance with the number of a plurality of patterns. Then, according to Embodiment 1, statistical processing is performed for respective calculated values, and the mode value is defined to be a dimension error amount (the first dimension error amount) representing the mesh region 50.

In the dimension error amount map generation step (S118), the map generation circuit 132 generates a dimension error amount map (a first dimension error amount map) of the whole of the inspection region 22 by using each dimension error amount (the first dimension error amount) in a plurality of discrete inspection stripes 20 (pre-scan regions 30). The map generation circuit 132 is an example of the first dimension error amount map generation unit. Since here only the value of each mesh region of a plurality of discrete inspection stripes 20 (pre-scan regions 30) is held as data, the map generation circuit 132 performs approximation (fitting) for the obtained mesh region value by using a polynomial in order to presume and estimate a value of other mesh region without data. Then, with respect to mesh regions with data, corresponding mesh region values are respectively input. By contrast, with respect to other mesh regions without data, estimated values are respectively input. Thus, a dimension error amount map (the first dimension error amount map) of the whole of the inspection region 22 is generated. Fitting using a polynomial is performed in this case, however, it is not limited thereto, and a value of other mesh region without data may be interpolated by a linear interpolation. The generated dimension error amount map (the first dimension error amount map, a dimension error amount map A) is stored in the magnetic disk drive 109, for example.

Figure 7:
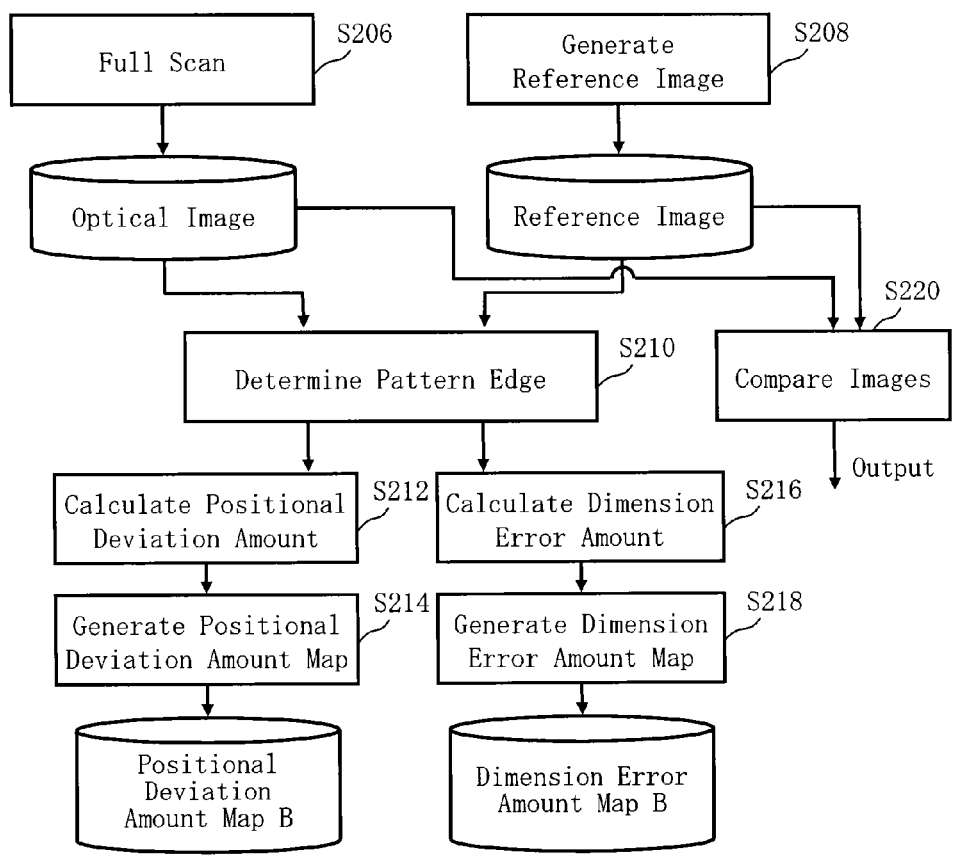
FIG. 7 is a flowchart showing another part of the main steps of the inspection method according to Embodiment 1.

FIG. 7 is a flowchart showing another part of the main steps of the inspection method according to Embodiment 1. FIG. 7 shows each step of measuring a positional deviation amount and a dimension error by a full scan and a step of inspecting a pattern defect in a series of steps of the inspection method according to Embodiment 1. As shown in FIG. 7, the method of measuring a positional deviation amount and a dimension error by a full scan according to Embodiment 1 executes a series of steps: a full scan step (S206), a reference image generation step (S208), a pattern edge determination step (S210), a positional deviation amount calculation step (S212), a positional deviation amount map generation step (S214), a dimension error amount calculation step (S216), and a dimension error amount map generation step (S218). Moreover, the pattern defect inspection method executes a series of steps: the full scan step (S206), the reference image generation step (S208), and a pixel comparison step (S220).

In the full scan step (S206), the full scan control circuit 146 controls each device so that an optical image may be acquired in order for each inspection stripe 20 of the whole of the inspecting inspection region 22 of the photo-mask 101, while relatively moving the photo diode array 105 and the XYθ table 102. The full scan control circuit 146 is an example of the second image acquisition control unit. For example, the image capturing is repeated in the FWD to BWD direction, meaning going in a reverse direction when advancing and returning. The pattern image focused on the photo diode array 105 is photoelectrically converted by each light receiving element of the photo diode array 105, and is further analog-to-digital (A/D) converted by the sensor circuit 106. Pixel data of each inspection stripe 20 is temporarily stored in the stripe pattern memory 123. Then, the pixel data is sent to the edge determination circuit 120 and the comparison circuit 108, with data which is output from the position circuit 107 and indicates the position of the photo-mask 101 on the XYθ table 102. Measurement data is 8-bit unsigned data, for example, and indicates a gray level (light intensity) of brightness of each pixel. The measurement data obtained by the full scan includes a positional deviation and a dimension error due to a temperature increase in the inspection apparatus 100.

In the reference image generation step (S208), the reference circuit 112 reads design data in order with respect to each inspection stripe 20 of the whole of the inspection region 22 from the magnetic disk drive 109 through the control computer 110. The read design data of the photo-mask 101 is converted into image data of binary values or multiple values to generate reference data (reference image). The reference data is 8-bit unsigned data, for example, and indicates a gray level (light intensity) of brightness of each pixel. Then, the reference data is sent to the edge determination circuit 120 and the comparison circuit 108.

In the pattern edge determination step (S210), the edge determination circuit 120 determines, for each mesh region described above, edges of a pattern (figure) with respect to the X direction, the Y direction, and a diagonal 45 degree direction (including 45, 135, 225, and 315 degrees), in pattern images respectively located in the optical image obtained from the sensor and the reference image. Then, a pattern edge (side) and another pattern edge (side) being a pair configuring the edge part are determined. Thus, the edge determination circuit 120 determines (detects) a pattern edge pair. In other words, the edge determination circuit 120 determines (detects) sides at both the ends which are factors to determine the dimension of each figure.

In the positional deviation amount calculation step (S212), the positional deviation amount calculation circuit 126 calculates a positional deviation amount (a second positional deviation amount) between a dimension of a figure in each optical image acquired when capturing images of the whole of the inspection region 22 and a dimension of a figure in each reference image corresponding to the optical image concerned. The positional deviation amount calculation circuit 126 is an example of the second positional deviation amount calculation unit. The method of calculating a positional deviation amount is the same as that of the pre-scan case described above.

In the positional deviation amount map generation step (S214), the map generation circuit 134 generates a positional deviation amount map (a second positional deviation amount map) of the whole of the inspection region 22 by using a positional deviation amount (the second positional deviation amount). The map generation circuit 134 is an example of the second positional deviation amount map generation unit. Since, in this case, the map generation circuit 134 has data of the value of each mesh region of the inspection stripes 20 in the whole of the inspection region 22, what is necessary is just to use the calculated values as they are. The generated positional deviation amount map (the second positional deviation amount map, a positional deviation amount map B) is stored in the magnetic disk drive 109, for example.

In the dimension error amount calculation step (S216), the dimension error amount calculation circuit 128 calculates a dimension error amount (a second dimension error amount) between a dimension of a figure in each optical image acquired when capturing images of the whole of the inspection region 22 and a dimension of a figure in each reference image corresponding to the optical image concerned. The dimension error amount calculation circuit 128 is an example of the second dimension error amount calculation unit. The method of calculating a dimension error amount is the same as that of the pre-scan case described above.

In the dimension error amount map generation step (S218), the map generation circuit 136 generates a dimension error amount map (a second dimension error amount map) of the whole of the inspection region 22 by using a dimension error amount (the second dimension error amount). The map generation circuit 136 is an example of the second dimension error amount map generation unit. Since, in this case, the map generation circuit 136 has data of the value of each mesh region of the inspection stripes 20 in the whole of the inspection region 22, what is necessary is just to use the calculated values as they are. The generated dimension error amount map (the second dimension error amount map, a dimension error amount map B) is stored in the magnetic disk drive 109, for example.

In the pixel comparison step (S220), the comparison circuit 108 (inspection unit) inputs, for each inspection stripe 20, measurement data (optical image) from the stripe pattern memory 123. On the other hand, reference data (reference image) is input from the reference circuit 112.

Then, position alignment is performed between the measurement data and the reference data. Each pixel data of the measurement data and reference pixel data of the reference data are compared, for each pixel, according to a predetermined algorithm in order to judge existence of a defect. For example, it is judged whether a pixel value difference between the measurement data and the reference data is within a threshold value or not. Then, the comparison result is output, for example, to the magnetic disk drive 109, the magnetic tape drive 115, the FD 116, the CRT 117, the pattern monitor 118, or the printer 119. Alternatively, it may be output to the outside.

Figure 8:
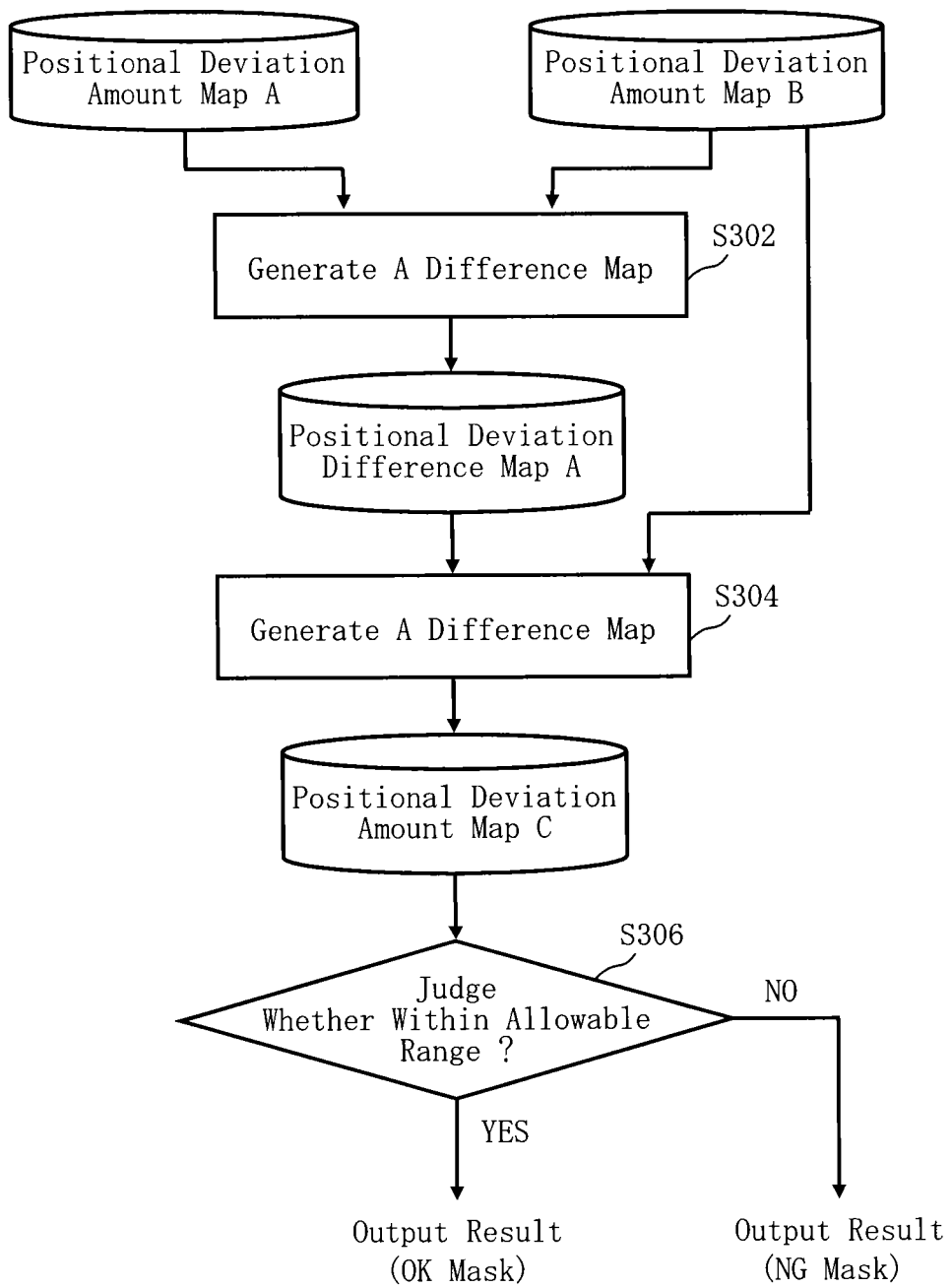
FIG. 8 is a flowchart showing another part of the main steps of the inspection method according to Embodiment 1.

FIG. 8 is a flowchart showing another part of the main steps of the inspection method according to Embodiment 1. FIG. 8 shows each step of the method of inspecting a positional deviation amount, which is performed after acquiring the positional deviation amount, in a series of steps of the inspection method according to Embodiment 1. As shown in FIG. 8, the inspection method for a positional deviation amount, performed after acquiring it, executes a series of steps: a difference map generation step (S302), a difference map generation step (S304), and a judgment step (S306).

In the difference map generation step (S302), the difference map generation circuit 152 calculates a difference between the positional deviation amount map (the first positional deviation amount map) acquired by a pre-scan and the positional deviation amount map (the second positional deviation amount map) acquired by a full scan in order to generate a positional deviation difference map (a first positional deviation difference map, a positional deviation difference map A). The difference map generation circuit 152 is an example of the first positional deviation difference map generation unit. In the positional deviation difference map (the first positional deviation difference map, the positional deviation difference map A), there is expressed a variation amount due to the inspection apparatus 100, such as a thermal expansion of the photo-mask 101, which is generated from the storage of energy of an inspection light irradiated on the photo-mask 101, and alternatively or additionally, a measurement error of the laser measuring system 122, which is generated from a change of air current inside the inspection apparatus 100 or various heat sources in the apparatus 100. In other words, a variation amount due to influence of a temperature change of the inspection apparatus 100 is expressed. The generated positional deviation difference map (the first positional deviation difference map, the positional deviation difference map A) is stored in the magnetic disk drive 109, for example.

In the difference map generation step (S304), the difference map generation circuit 153 calculates a difference between the positional deviation amount map (a second positional deviation amount map) acquired by a full scan and the positional deviation difference map (a first positional deviation difference map, a positional deviation difference map A) in order to generate a corrected positional deviation amount map (a third positional deviation amount map, a positional deviation amount map C). The difference map generation circuit 153 is an example of the third positional deviation amount map generation unit. In the generated corrected positional deviation amount map (the third positional deviation amount map, the positional deviation amount map C), there is defined a positional deviation amount obtained by excluding a variation amount due to influence of the environmental change in the apparatus, such as a temperature change of the inspection apparatus 100, from the positional deviation amount map acquired by a full scan. In other words, the positional deviation amount of the pattern itself, formed on the photo-mask 101, is shown. The generated positional deviation amount map (the third positional deviation amount map, the positional deviation amount map C) is stored in the magnetic disk drive 109, for example.

In the judgment step (S306), the judging circuit 156 judges whether there is a value exceeding an allowable value, in the values defined in the positional deviation amount map (the third positional deviation amount map, the positional deviation amount map C) or not. The judging circuit 156 is an example of a positional deviation amount judging unit. Then, the judgment result with respect to the positional deviation amount is output, for example, to the magnetic disk drive 109, the magnetic tape drive 115, the FD 116, the CRT 117, the pattern monitor 118, or the printer 119. Alternatively, it may be output to the outside. In particular, the CRT 117, the pattern monitor 118, or the printer 119 outputs a judgment result visually to a user by displaying it. The CRT 117, the pattern monitor 118, or the printer 119 serves as an example of an output unit. If each map value defined in the positional deviation amount map (the third positional deviation amount map, the positional deviation amount map C) is within an allowable value, it is judged to be an allowable mask. By contrast, if there is a map value exceeding the allowable value, it is judged to be an NG mask. In other words, it is possible to judge that the uniformity of the positional deviation amount in the mask surface is out of the allowable range. This NG mask is evaluated as an NG mask even if a pattern defect is within the allowance when performing a pixel comparison.

Figure 9:
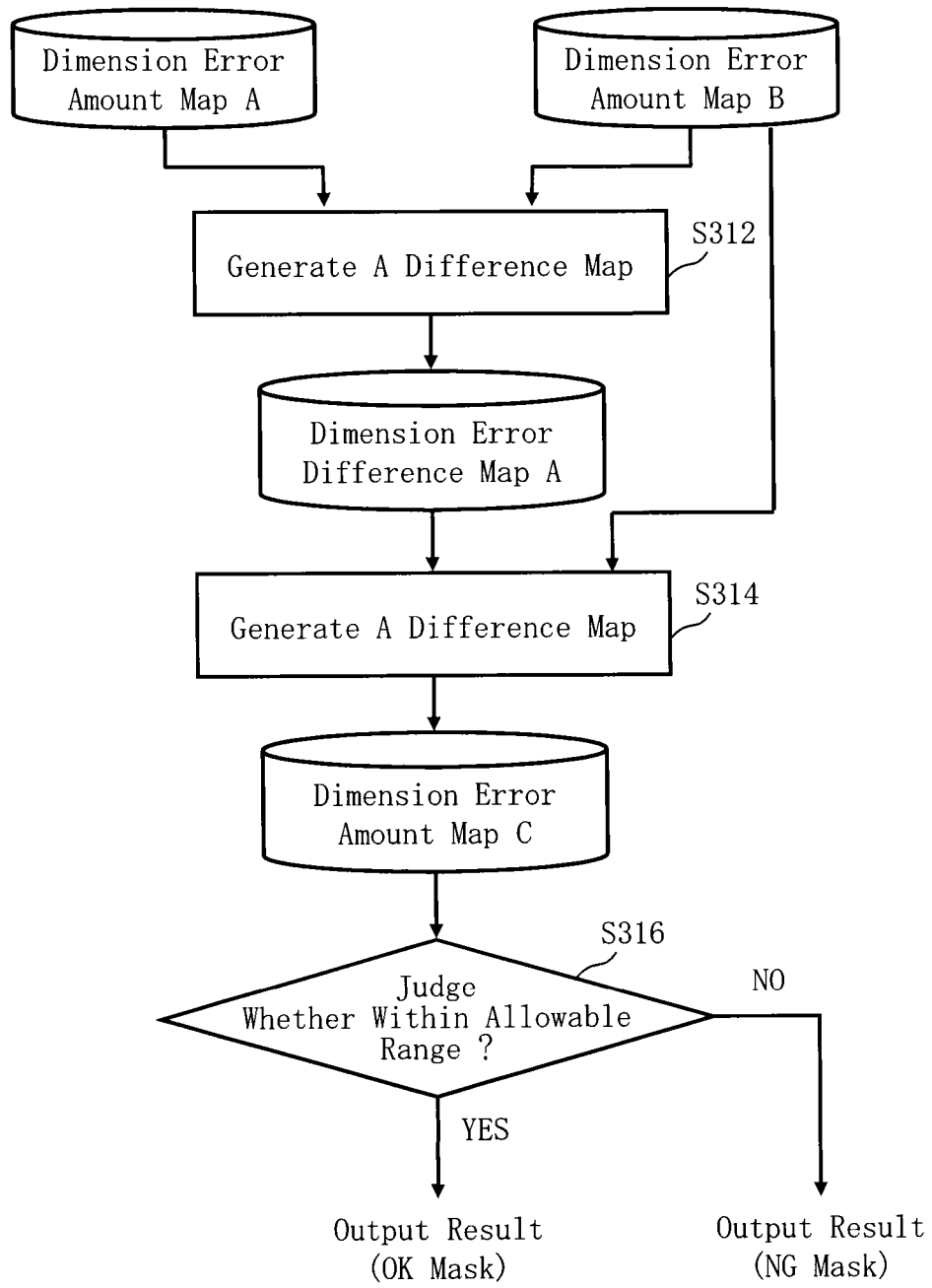
FIG. 9 is a flowchart showing another part of the main steps of the inspection method according to Embodiment 1.

FIG. 9 is a flowchart showing another part of the main steps of the inspection method according to Embodiment 1. FIG. 9 shows each step of the method of inspecting a dimension error amount, which is performed after acquiring the dimension error amount, in a series of steps of the inspection method according to Embodiment 1. As shown in FIG. 9, the inspection method for a dimension error amount, performed after acquiring it, executes a series of steps: a difference map generation step (S312), a difference map generation step (S314), and a judgment step (S316).

In the difference map generation step (S312), the difference map generation circuit 154 calculates a difference between the dimension error amount map (the first dimension error map) acquired by a pre-scan and the dimension error map (the second dimension error map) acquired by a full scan in order to generate a dimension error difference map (a first dimension error difference map, a dimension error difference map A). The difference map generation circuit 154 is an example of the first dimension error difference map generation unit. In the dimension error difference map (the first dimension error difference map, the dimension error difference map A), there is expressed a variation amount due to the inspection apparatus 100, such as a thermal expansion of the photo-mask 101, which is generated from the storage of energy of an inspection light irradiated on the photo-mask 101, and alternatively or additionally, a measurement error of the laser measuring system 122, which is generated from a change of air current inside the inspection apparatus 100 or various heat sources in the apparatus 100. In other words, a variation amount due to influence of a temperature change of the inspection apparatus 100 is expressed. The generated dimension error difference map (the first dimension error difference map, the dimension error difference map A) is stored in the magnetic disk drive 109, for example.

In the difference map generation step (S314), the difference map generation circuit 155 calculates a difference between the dimension error amount map (a second dimension error amount map) acquired by a full scan and the dimension error difference map (a first dimension error difference map, a dimension error difference map A) in order to generate a corrected dimension error amount map (a third dimension error amount map, a dimension error amount map C). The difference map generation circuit 155 is an example of the third dimension error amount map generation unit. In the generated corrected dimension error amount map (the third dimension error amount map, the dimension error amount map C), there is defined a dimension error amount obtained by excluding a variation amount due to influence of the environmental change in the apparatus, such as a temperature change of the inspection apparatus 100, from the dimension error amount map acquired by a full scan. In other words, the dimension error amount of the pattern itself, formed on the photo-mask 101, is shown. The generated dimension error amount map (the third dimension error amount map, the dimension error amount map C) is stored in the magnetic disk drive 109, for example.

In the judgment step (S316), the judging circuit 158 judges whether there is a value exceeding an allowable value, in the values defined in the dimension error amount map (the third dimension error amount map, the dimension error amount map C) or not. The judging circuit 158 is an example of a dimension error amount judging unit. Then, the judgment result with respect to the dimension error amount is output, for example, to the magnetic disk drive 109, the magnetic tape drive 115, the FD 116, the CRT 117, the pattern monitor 118, or the printer 119. Alternatively, it may be output to the outside. In particular, the CRT 117, the pattern monitor 118, or the printer 119 outputs a judgment result visually to a user by displaying it. The CRT 117, the pattern monitor 118, or the printer 119 serves as an example of an output unit. If each map value defined in the dimension error amount map (the third dimension error amount map, the dimension error amount map C) is within an allowable value, it is judged to be an allowable mask. By contrast, if there is a map value exceeding the allowable value, it is judged to be an NG mask. In other words, it is possible to judge that the uniformity of the dimension error amount in the mask surface is out of the allowable range. This NG mask is evaluated as an NG mask even if a pattern defect is within the allowance when performing a pixel comparison.

Focusing on that the variation described above can be ignored if the operation time is short, in advance of inspecting the whole surface of the mask, the whole mask surface is pre-scanned discretely in a short time to take data on distribution of pattern positional deviation and pattern dimension errors in a state without influence of temperature change. Then, later, inspection of the whole mask surface is performed and data on distribution of pattern positional deviation and pattern dimension errors is taken. The error distribution on these positional deviation error and dimension error is to be corrected by using the already taken distribution data in a state without influence of temperature change.

Thus, according to Embodiment 1, it is possible to acquire highly reliable error distribution data of the whole mask surface by correcting distribution data on pattern positional deviation and pattern dimension errors of the whole mask surface, which is taken in tandem with the whole mask inspection, by using distribution data in a state without influence of a temperature change. Accordingly, there can be provided an inspection apparatus and an inspection method capable of measuring uniformity in a mask surface, which is conventionally needed to be measured by another device.

It is suitable for the mesh region described above to be a frame region having an appropriate dimension to be treated in a process of comparison judgment processing of the inspection apparatus. As an example of the mesh dimension, it is preferable to set it to be a quadrangular region (a square region or a rectangular region) of a side of about 30 to 50 μm. Assuming that square contact hole patterns each having a side of 200 nm are arranged at a pitch of 500 nm, there would be about $59^2=3481$ patterns in the quadrangular region of 30 μm square. On the other hand, if a pattern is processed by a pixel of 50 nm, the side at the end part in the X direction and the side at the end part in the Y direction of the contact hole of 200 nm square configure a pattern edge pair respectively over four pixels theoretically, two or three pixels practically. Therefore, it is possible to perform pattern dimension calculation and pattern position calculation over two or three pixels. What is needed is to specify positions of pixels being an edge pair in the pattern edge pair, and calculate a distance between the pixels when performing a pattern dimension calculation or calculate an intermediate position being the exact middle between the pixels when performing a pattern position calculation. For this reason, it is possible to perform pattern edge pair calculation of four points totally, namely two points respectively in the X and Y directions for each contact hole pattern. Therefore, 13924 (=3481×4) pattern positions and line width measurement values can be acquired in a quadrangular region (frame region) of 30 μm square. For the positional deviation amount data and line width dimension error data acquired by the processing described above, statistical processing is performed in the mesh region. Then, the highest frequency (mode) value is to be a positional deviation value or a line width error value representing the mesh region. Assuming that the inspection region 22 is a 100 mm square, for example, if there are approximately 20×20 to 100×100 measurement places in the X and Y directions respectively, it would be sufficient to generate a significant map. Accordingly, for example, when a mesh region of 30 μm square is set, it is enough to perform calculation at about 1 to 5 mm intervals in the mesh region, for example.

Therefore, when performing a full scan, although it is preferable to calculate pattern positional deviation amounts and dimension error amounts in all the mesh regions of images acquired with respect to the whole surface of the inspection region 22, it is also preferable to perform calculation in the mesh regions described above which are at about 1 to 5 mm intervals, for example, with respect to the X direction and the Y direction. Further, assuming that the inspection region 22 is a 100 mm square, for example, it is preferable to perform calculation in the mesh regions located at coordinates obtained by equally dividing the inspection region 22 by 20 to 100. In other words, when performing a full scan, it is acceptable, with respect to the dividing direction (Y direction) of the inspection stripe 20, to judge whether the inspection stripe 20 corresponds to the coordinates obtained by equally dividing the inspection region 22 by 20 to 100 or not, and to calculate pattern positional deviation amounts and dimension error amounts of the corresponding inspection stripes 20. Then, a positional deviation amount map and a dimension error amount map of the inspection mask can be acquired by mapping the calculated values.

At the time of a full scan and/or a pre-scan, there is a case where no pattern edge is included in a mesh region in the imaged inspection stripe 20. Moreover, when performing calculation in the mesh regions described above which are at about 1 to 5 mm intervals, for example, in the X and Y directions respectively, there is a case where a mesh region including no pattern edge is a region to be calculated. In that case, a mesh region which includes a pattern edge and is closest to the mesh region including no pattern edge is to be a calculation region instead of the mesh region with no pattern edge. If the inspection region 22 is a 100 mm square, for example, the length in the longitudinal direction (X direction) of the inspection stripe 20 is also 100 mm. Then, what is necessary is to treat mesh regions located at the coordinates obtained by equally dividing the inspection region 22 by 20 to 100 as targets of calculation. In stead of a mesh region including no pattern edge in the mesh regions calculated at such intervals described above, a mesh region which includes a pattern edge and is closest to the mesh region without pattern edge can be used.

Moreover, the time required for calculating each mesh region in the imaged inspection stripes 20 (pre-scan regions 30) is extremely short compared with the time required for imaging with a sensor while running the stage. Therefore, even when the running is performed while thinning out the inspection stripes 20 to be imaged in pre-scanning, the running of the pre-scanning is not affected by the calculation time in the mesh region. Thus, the time necessary for a pre-scan can be short compared with that for a full scan, and therefore, the scanning can be completed before being affected by an environmental change, such as a temperature increase, in the apparatus.

The positional deviation amount map and the dimension error amount map according to Embodiment 1 can be criteria to determine mask evaluation, which is different from the one conventionally performed based on a local shape defect of the mask pattern. Therefore, even when it is judged by the conventional mask shape inspection that there is no defect, if it is judged according to the map that the uniformity of the whole surface of the mask is poor, the inspection mask concerned is judged being defective. The indication of judging the uniformity to be poor is the case in which a positional deviation amount of a pattern in the whole mask surface is a peak-to-peak value, such as there being an error of about 20 nm, for example, or there being a place whose maximum line-width error amount exceeds 20 nm in the whole mask surface.

Although the criterion for determination is expressed by a value in nanometers [nm] in the example described above, there is another method of determining the criterion of an allowable uniformity of the surface by using a ratio (specifying a percent value) with respect to a typical line width determined by the device technology node in which the inspection mask is used. For example, the method is to determine the line width allowable value to be 10% of the line width. Assuming a device technology node having a half-pitch (hp) of 28 nm, an allowable value of a positional deviation amount and a line width of the typical line width (112 nm) on a tetraploid mask is determined to be 10% of the line width, that is 11.2 nm. Although there are various dimension patterns on the mask, 10% is applied to any pattern. Accordingly, the allowable error dimension at a large pattern dimension place is large, and that at a small pattern dimension place is small.

Thus, even when there is no pattern shape defect, if a pattern positional deviation or pattern line width error of the mask surface exceeds an allowable value, the mask is determined to be a failure, thereby executing a more highly precise mask inspection compared with the conventional case.

According to Embodiment 1, the mask which has no pattern shape defect and has passed the evaluation of pattern positional deviation and line width error is sent to the next step of wafer exposure. The wafer exposure apparatus performs reduced projection of the original mask, for example, at a projection magnification of ¼ to print the wafer. In the latest wafer exposure apparatuses, there is a type that can form a ring belt shaped light source or an anisotropic light source, instead of a single point light source. When information obtained by measuring the distribution of the whole mask surface according to 1 Embodiment 1 is input into such an exposure apparatus capable of controlling a light source shape, it becomes possible to perform correction of a light intensity distribution of the light source, thereby balancing out the data of a positional deviation and a line-width distribution in the mask surface, and thus obtaining a more accurate wafer exposure image. That is, a pattern line width formed on the wafer surface can be a fixed width having a higher uniformity at the whole surface by controlling the light intensity of the light source for exposure, which corresponds to a region of a narrow pattern line width on the mask, to be high, and controlling the light intensity of the light source for exposure, which corresponds to a region of a wide pattern line width on the mask, to be low. Moreover, with respect to pattern positional deviation on the mask, it is possible to form a pattern position on the wafer surface to be an ideal position and line width in accordance with the design by controlling a luminescent spot position of the point light source to be eccentrically shifted such that the pattern deviation is balanced out, by an exposure apparatus capable of controlling a light source shape.

Thus, even when a mask has passed the mask inspection, since it is possible to perform a suitable correction in the wafer exposure/transfer step by using information on pattern positional deviation, line width error positional deviation, and a line width distribution within the allowable range, thereby forming a more highly precise wafer pattern.

Furthermore, even when a mask has failed the mask inspection because error of its pattern positional deviation line width slightly exceeds the allowable value, it is possible to form a pattern position and a line width to be ideal ones in accordance with the design by performing a suitable correction in the wafer exposure/transfer step by using information on pattern positional deviation, line width error positional deviation, and a line width distribution. Thereby, the number of masks having failed the inspection can be reduced, and the manufacture yield can be increased.

It is considered that the cause of generating a pattern positional deviation and a line-width error of a manufactured mask is a change of stability of the mask writing apparatus and a change of the mask manufacturing process at the time of writing a pattern by the mask writing apparatus. If a mask surface distribution map according to Embodiment 1 has a distribution tendency which is common to a plurality of masks and which possesses reproducibility, such a tendency may be offset by correction performed by the writing apparatus. For example, in the region where the line width is formed slightly narrowly, the pattern line width to be written is corrected to be wide in advance, or in the region where pattern positional deviation is generated, a pattern is shifted in the reverse direction in advance.

In the present technique described above, a mask pattern image can be calculated using not only an image acquired using transmitted light but also a reflected image. Moreover, the present technique described above is effective for inspection of a reflective mask for EUV exposure in addition to for inspection of a mask for optical lithography.

According to Embodiment 1, as described above, it is possible to inspect at least uniformity of position accuracy of patterns formed on the mask.

In the above description, processing contents or operation contents of what is expressed by the term "unit" or "circuit" can be configured by a computer operable program. Alternatively, they may be implemented not only by a program being software but also by a combination of hardware and software, or further, by a combination of hardware and firmware. When configured by a program, the program is stored in a recording medium, such as the magnetic disk drive 109, the magnetic tape unit 115, the FD 116, or the ROM (read only memory). For example, each of the position circuit 107, the comparison circuit 108, the reference circuit 112, the autoloader control circuit 113, the table control circuit 114, the edge determination circuit 120, the positional deviation amount calculation circuits 125 and 126, the dimension error amount calculation circuits 124 and 128, the map generation circuits 131, 132, 134, and 136, the pre-scan region judging circuit 140, the setting circuit 142, the pre-scan control circuit 144, the full scan control circuit 146, the difference map generation circuits 152, 153, 154, and 155, and the judging circuits 156 and 158 may be configured by an electric circuit. Alternatively, they may be implemented as software to be processed by the control computer 110, or implemented by a combination of electric circuits and software.

Moreover, although the example described above explains the case of generating a reference image from design data, based on die-to-database inspection, it is not limited thereto.

Figure 10:
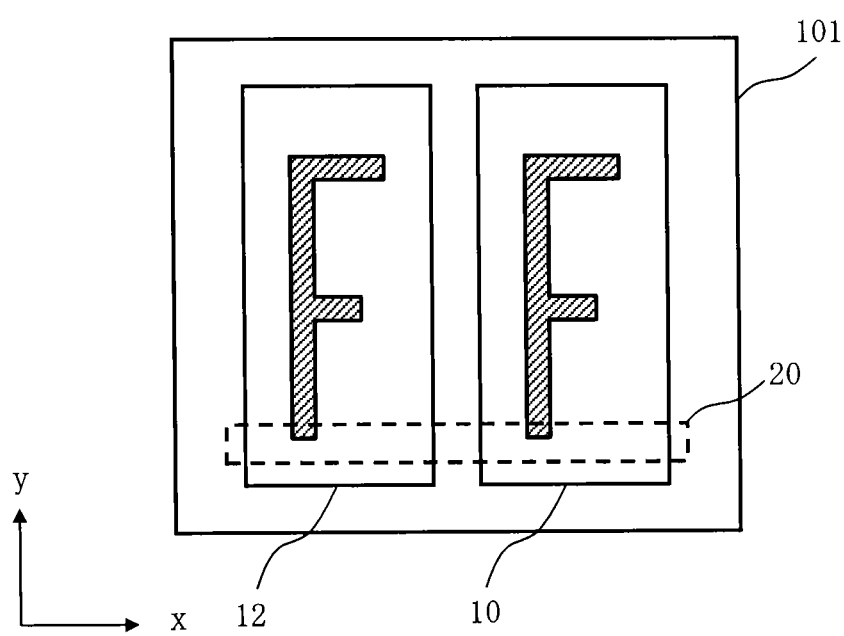
FIG. 10 is a schematic diagram for explaining a die-to-die inspection.

FIG. 10 is a schematic diagram for explaining a die-to-die inspection. In FIG. 10, a plurality of pattern regions 10 and 12 (regions to be inspected, namely inspection regions) written by using the same design pattern are formed on the photo-mask 101. The whole composed of the two pattern regions 10 and 12 is virtually divided into a plurality of inspection stripes shown in FIG. 2. Then, optical image data (measurement data) is acquired for each inspection stripe by the optical image acquisition unit 150. Therefore, images of both the pattern regions 10 and 12 are included in measurement data of one inspection stripe. If a positional deviation amount and a dimension error amount are similarly calculated treating one image of the measured pattern regions 10 and 12 as an optical image described above, and the other one as a reference image, it is possible to apply Embodiment 1, based on the die-to-die inspection.

Referring to specific examples, Embodiments have been described above. However, the present invention is not limited to these examples. For example, although the inspection apparatus using a transmitting optical system and a transmission light of the photo-mask 101 has been described above, it is not limited thereto. The present invention is also effective for the inspection apparatus using a reflecting optical system and a reflection light of the photo-mask 101.

While the apparatus configuration, control method, etc. not directly necessary for explaining the present invention are not described, some or all of them may be suitably selected and used when needed. For example, although description of the configuration of a control unit for controlling the writing apparatus 100 is omitted, it should be understood that some or all of the configuration of the control unit is to be selected and used appropriately when necessary.

In addition, any other pattern inspection apparatus and a method thereof that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An inspection apparatus comprising:
  a stage on which an inspection target object with a plurality of figure patterns formed thereon is placed and which is movable;
  a light source that emits an inspection light;
  a sensor that captures an optical image of the plurality of figure patterns formed on the inspection target object by using the inspection light while moving relatively to the stage; and
  processing circuitry configured to:
    virtually divide a whole of an inspection region of the inspection target object into stripe regions, each of the stripe regions including a corresponding one of a plurality of discrete small regions, and each of the stripe regions and the plurality of discrete small regions having a same width as a width of the whole of the inspection region;

perform a pre-scan such that the pre-scan is completed before being affected by a temperature change in the inspection apparatus, by controlling to acquire an optical image in each of the plurality of discrete small regions in order, while relatively moving the sensor and the stage without performing imaging with respect to a region located between each of the plurality of discrete small regions;

perform a full-scan by controlling to acquire an optical image in each of the stripe regions in the whole of the inspection region of the inspection target object in order while relatively moving the sensor and the stage;

calculate a first positional deviation amount between a dimension of a figure in each optical image acquired when capturing images of the plurality of discrete small regions in relation to the pre-scan and a dimension of a figure in a reference image corresponding to the each optical image;

generate a first positional deviation amount map of the whole of the inspection region by using the first positional deviation amount of each of the plurality of discrete small regions;

calculate a second positional deviation amount between a dimension of a figure in each optical image acquired when capturing images of the whole of the inspection region in relation to the full-scan and a dimension of a figure in a reference image corresponding to the each optical image;

generate a second positional deviation amount map of the whole of the inspection region by using the second positional deviation amount;

generate a first positional deviation difference map by calculating a difference between the first positional deviation amount map and the second positional deviation amount map;

generate a third positional deviation amount map by calculating a difference between the second positional deviation amount map and the first positional deviation difference map, the third positional deviation amount map corresponding to a corrected positional deviation amount man that compensates for the temperature change;

judge existence of a value exceeding an allowable value, in values defined by the third positional deviation amount map; and output a judgment result to indicate whether a mask is allowable, wherein the plurality of discrete small regions are disposed apart from each other at a particular distance to suppress bias of the inspection region, and are provided within the stripe regions; and an area of one of the plurality of discrete small regions is less than an area of the region that is located between two consecutive discrete small regions from among the plurality of discrete small regions.

2. The apparatus according to claim 1, wherein the processing circuitry is further configured to:

calculate a first dimension error amount between the dimension of the figure in the each optical image acquired when capturing images of the plurality of discrete small regions in relation to the pre-scan and the dimension of the figure in the reference image corresponding to the each optical image;

generate a first dimension error amount map of the whole of the inspection region by using the first dimension error amount of each of the plurality of discrete small regions;

calculate a second dimension error amount between the dimension of the figure in the each optical image acquired when capturing images of the whole of the inspection region in relation to the full-scan and the dimension of the figure in the reference image corresponding to the each optical image;

generate a second dimension error amount map of the whole of the inspection region by using the second dimension error amount;

generate a first dimension error difference map by calculating a difference between the first dimension error amount map and the second dimension error amount map;

generate a third dimension error amount map by calculating a difference between the second dimension error amount map and the first dimension error difference map; and judge existence of a value exceeding an allowable value, in values defined by the third dimension error amount map.

3. The apparatus according to claim 2, wherein the processing circuitry is further configured to output a judgment result with respect to a dimension error amount.

4. The apparatus according to claim 1, wherein the stripe regions extend in a predetermined direction.

5. The apparatus according to claim 1, wherein:

the processing circuitry is further configured to:

judge whether a figure pattern exists in each of the stripe regions, and when a figure pattern exists in each of all of judged stripe regions, set the all of the judged stripe regions, as the plurality of discrete small regions, and, when a figure pattern does not exist in each of some or all of the judged stripe regions, set stripe regions each including a figure pattern and stripe regions each inducing a figure pattern, being closest to a stripe region including no figure pattern, and serving instead of the stripe region including no figure pattern, as the plurality of discrete small regions.

6. A pattern inspection method for an inspection apparatus including a sensor and a stage, the pattern inspection method comprising:

virtually dividing a whole of an inspection region of an inspection target object into stripe regions, each of the stripe regions including a corresponding one of a plurality of discrete small regions, and each of the stripe regions and the plurality of discrete small regions having a same width as a width of the whole of the inspection region;

performing a pre-scan such that the pre-scan is completed before being affected by a temperature change in the inspection apparatus, by controlling to acquire an optical image in each of the plurality of discrete small regions in order, while relatively moving the sensor and the stage without performing imaging with respect to a region located between each of the plurality of discrete small regions;

performing a full-scan by controlling to acquire an optical image in each small region of the stripe regions in the whole of the inspection region of the inspection target object in order while relatively moving the sensor and the stage;

calculating a first positional deviation amount between a dimension of a figure in each optical image acquired when capturing images of the plurality of discrete small regions in relation to the pre-scan and a dimension of a figure in a reference image corresponding to the each optical image;

generating a first positional deviation amount map of the whole of the inspection region by using the first positional deviation amount of each of the plurality of discrete small regions;

generating a second positional deviation amount map by using data acquired by the full-scan;

generating a first positional deviation difference map by calculating a difference between the first positional deviation amount map and the second positional deviation amount map;

generating a third positional deviation amount map from the first positional deviation difference map and the second positional deviation amount map, the third positional deviation amount map corresponding to a corrected positional deviation amount map that compensates for the temperature change;

judging existence of a value exceeding an allowable value, in values defined by the third positional deviation amount map; and outputting a judgement result to indicate whether a mask is allowable, wherein the plurality of discrete small regions are disposed apart from each other at a particular distance to suppress bias of the inspection region, and are provided within the stripe regions; and an area of one of the plurality of discrete small regions is less than an area of the region that is located between two consecutive discrete small regions from among the plurality of discrete small regions.

7. The method according to claim 6, wherein, in the second positional deviation amount map, there is defined a second positional deviation amount between a dimension of a figure in each optical image acquired when capturing images of the whole of the inspection region in relation to the full-scan and a dimension of a figure in a reference image corresponding to the each optical image.

8. The method according to claim 6, further comprising:
generating a first dimension error amount map by using data acquired by the pre-scan;
generating a second dimension error amount map by using data acquired by the full-scan;
generating a first dimension error amount difference map by calculating a difference between the first dimension error amount map and the second dimension error amount map;
generating a third dimension error amount map from the first dimension error amount difference map and the second dimension error amount map; and
judging existence of a value exceeding an allowable value, in values defined by the third dimension error amount map.

9. The method according to claim 8, wherein, in the first dimension error amount map, there is defined a first dimension error amount between the dimension of the figure in the each optical image acquired when capturing images of the plurality of discrete small regions and the dimension of the figure in the reference image corresponding to the each optical image.

10. The method according to claim 8, wherein, in the second dimension error amount map, there is defined a second dimension error amount between the dimension of the figure in the each optical image acquired when capturing images of the whole of the inspection region and the dimension of the figure in the reference image corresponding to the each optical image.

11. The method according to claim 9, wherein the stripe regions extend in a predetermined direction.

12. The method according to claim 9, further comprising:
judging whether a figure pattern exists in each of the stripe regions; and
setting, when a figure pattern exists in each of all of judged stripe regions, the all of the judged stripe regions, as the plurality of discrete small regions, and, when a figure pattern does not exist in each of some or all of the judged stripe regions, stripe regions each including a figure pattern and stripe regions each including a figure pattern, being closest to a stripe region including no figure pattern, and serving instead of the stripe region including no figure pattern, as the plurality of discrete small regions.

13. The method according to claim 9, further comprising:
calculating a first positional deviation amount between the dimension of the figure in the each optical image acquired when capturing images of the plurality of discrete small regions and the dimension of the figure in the reference image corresponding to the each optical image;
calculating a second positional deviation amount between the dimension of the figure in the each optical image acquired when capturing images of the whole of the inspection region and the dimension of the figure in the reference image corresponding to the each optical image; and
outputting a judgment result with respect to a dimension error amount.

14. A pattern inspection method for an inspection apparatus including a sensor and a stage, the pattern inspection method comprising:
virtually dividing a whole of an inspection region of the inspection target object into stripe regions, each of the stripe regions including a corresponding one of a plurality of discrete small regions, and each of the stripe regions and the plurality of discrete small regions having a same width as a width of the whole of inspection region;
performing a pre-scan such that the pre-scan is completed before being affected by a temperature change in the inspection apparatus, by controlling to acquire an optical image in each of the plurality of discrete small regions in order, while relatively moving the sensor and the stage without performing imaging with respect to a region located between each of the plurality of discrete small regions;
performing a full-scan by controlling to acquire an optical image in each of the stripe regions in the whole of the inspection region of the inspection target object in order while relatively moving the sensor and the stage;
generating a first dimension error amount map by using data acquired by the pre-scan;
generating a second dimension error amount map by using data acquired by the full-scan;
generating a first dimension error amount difference map by calculating a difference between the first dimension error amount map and the second dimension error amount map;
generating a third dimension error amount map from the first dimension error amount difference map and the second dimension error amount map, the third dimension error amount map corresponding to a corrected dimension error amount map that compensates for the temperature change;

judging existence of a value exceeding an allowable value, in values defined by the third dimension error amount map; and outputting a judgment result to indicate whether a mask is allowable, wherein the plurality of discrete small regions are disposed apart from each other at a particular distance to suppress bias of the inspection region, and are provided within the stripe regions; and an area of one of the plurality of discrete small regions is less than an area of the region that is located between two consecutive discrete small regions from among the plurality of discrete small regions.

15. The method according to claim 14, wherein, in the first dimension error amount map, there is defined a first dimension error amount between a dimension of a figure in each optical image acquired when capturing images of the plurality of discrete small regions and a dimension of a figure in a reference image corresponding to the each optical image.

16. The method according to claim 14, wherein, in the second dimension error amount map, there is defined a second dimension error amount between a dimension of a figure in each optical image acquired when capturing images of the whole of the inspection region and a dimension of a figure in a reference image corresponding to the each optical image.

17. The method according to claim 14, wherein the plurality of stripe regions extend in a predetermined direction.

18. The method according to claim 14, further comprising:

judging whether a figure pattern exists in each of the stripe regions; and setting, when a figure pattern exists in each of all of judged stripe regions, the all of the judged stripe regions, as a plurality of discrete small regions, and, when a figure pattern does not exist in each of some or all of the judged stripe regions, stripe regions each including a figure pattern and stripe regions each including a figure pattern, being closest to a stripe region including no figure pattern, and serving instead of the stripe region including no figure pattern, as the plurality of discrete small regions.

19. The apparatus according to claim 1, wherein the processing circuitry is further configured to determine, from the plurality of discrete small regions, a pre-scan region to be pre-scanned.

20. The apparatus according to claim 1, wherein a total imaging time of the pre-scan is less than a total imaging time of the full-scan.

* * * * *